United States Patent [19]
Shemet

[11] Patent Number: 5,382,160
[45] Date of Patent: Jan. 17, 1995

[54] DENTAL MATRIX WITH RETENTION AND LOCKING MECHANISM

[76] Inventor: Arthur Shemet, 133 E. 58th St., Suite 308, New York, N.Y. 10022

[21] Appl. No.: 125,121

[22] Filed: Sep. 23, 1993

[51] Int. Cl.⁶ ............................................. A61C 5/04
[52] U.S. Cl. ........................................................ 433/39
[58] Field of Search ........................ 433/39, 40, 41, 23

[56]             References Cited
           U.S. PATENT DOCUMENTS

| | | | |
|---|---|---|---|
| 713,273 | 11/1902 | Alexander | 433/40 |
| 1,255,109 | 1/1918 | Russ | 433/39 |
| 1,669,231 | 5/1928 | Curran | 433/39 |
| 2,007,517 | 7/1935 | Boyd et al. | 433/23 |
| 2,035,135 | 10/1935 | LeBow | 433/39 |
| 2,353,747 | 7/1944 | Morrison | 433/39 |
| 3,795,981 | 3/1974 | Franklin et al. | 433/39 |
| 3,829,975 | 8/1974 | Balson | 433/39 |
| 3,854,210 | 12/1974 | Franklin et al. . | |
| 4,024,643 | 5/1977 | Eisenberg | 433/39 |
| 4,303,389 | 12/1981 | Salsarulo . | |
| 4,482,319 | 11/1984 | Patch . | |
| 4,553,937 | 11/1985 | Ropers | 433/39 |
| 4,718,849 | 1/1988 | von Weissenfluh | 433/39 |
| 4,720,264 | 1/1988 | Lazarus . | |
| 4,781,583 | 11/1988 | Lazarus . | |
| 4,824,365 | 4/1989 | von Weissenfluh | 433/40 |
| 4,909,736 | 3/1990 | Ritter . | |
| 4,997,367 | 3/1991 | Kassel | 433/39 |
| 5,035,615 | 7/1991 | Din . | |

FOREIGN PATENT DOCUMENTS 107441  6/1939  Australia ............................... 433/23

Primary Examiner—Cary E. O'Connor
Attorney, Agent, or Firm—Levisohn, Lerner & Berger

[57]            ABSTRACT

A dental matrix for use in dental procedures performed in a patient's mouth has a wide, flat central portion and at least one outwardly extending arm having ratchet-like teeth. The central portion has a slot cut therein to cooperate with the ratchet teeth to ensure the easy ability to tighten the matrix around the tooth. The ratchet teeth lie in the same plane as the central portion.

9 Claims, 1 Drawing Sheet

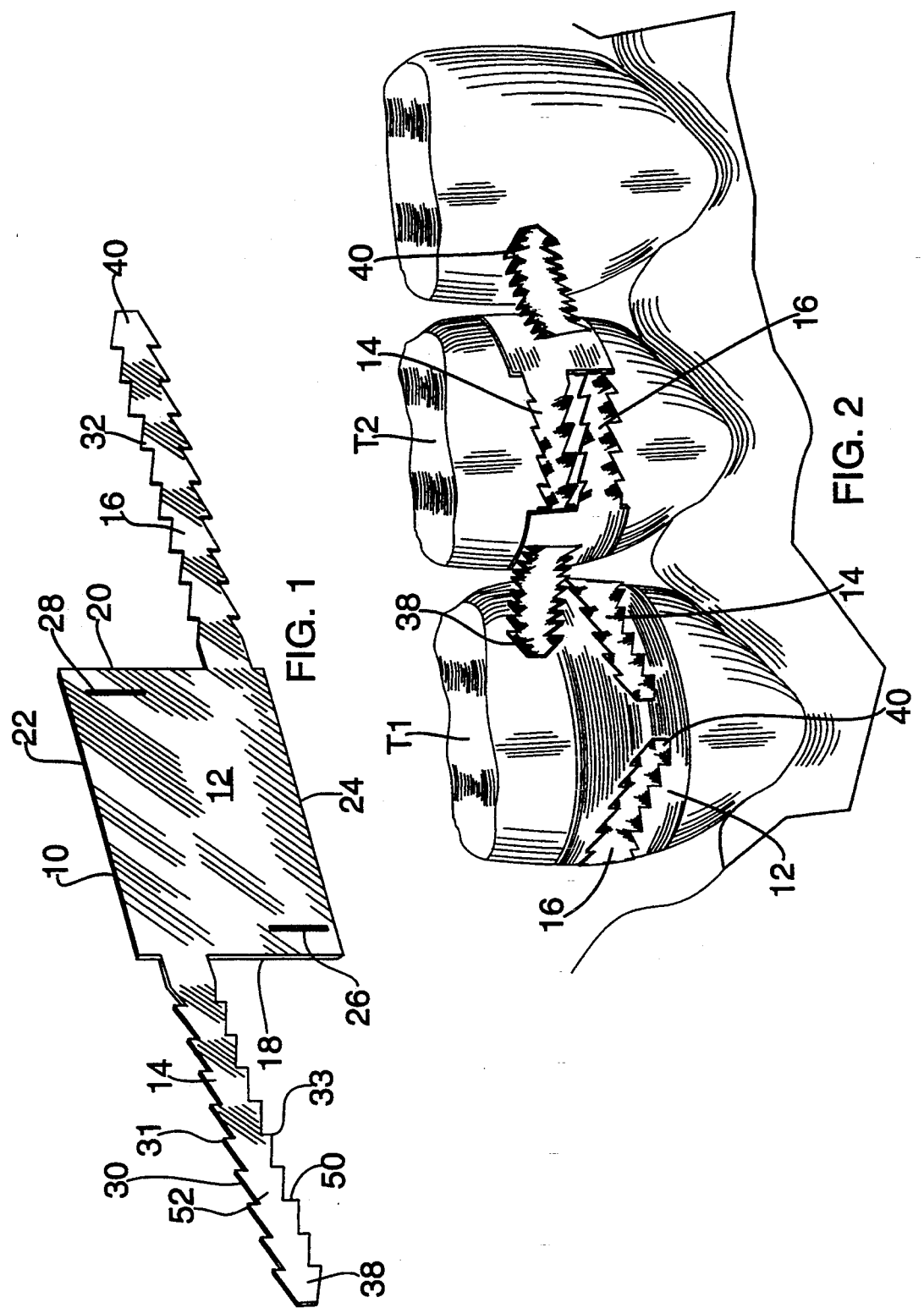

DENTAL MATRIX WITH RETENTION AND LOCKING MECHANISM

BACKGROUND OF THE INVENTION

The present invention relates to a dental matrix and more particularly, to a thin and clear plastic dental matrix for use in restoration procedures on tooth structure. The present invention is intended to be used by a dentist in connection with tooth-related procedures. The present invention is a dental matrix which facilitates the placement and holding of dental restorative compositions in and against the pre-drilled tooth structure. The present invention is directed to a clear plastic thin film which is capable of substantially surrounding the tooth structure. Laterally extending arms, cooperating with slots, allow the matrix to be easily and quickly drawn tightly around the tooth structure by the dentist independent of the location of the surface being worked upon. The present invention provides a mechanism for locking, in place, the dental matrix about the tooth structure and, furthermore, allows for a plurality of teeth to be simultaneously worked upon since the holding and locking mechanism of the dental matrix is extremely thin and, therefore, two adjacent teeth can be worked upon, each of which being provided with the dental matrix, without interference with one another.

DESCRIPTION OF THE PRIOR ART

U.S. Pat. No. 4,718,849 relates to a sheet-like dental die. As described and disclosed therein, the dental die is made of a material permeable to light and to UV rays. That matrix is intended to be inert with respect to the composite material so as to not bind to hardenable filling synthetic materials by radiation. So, too, the present invention is intended to be made from similar material. The purpose of utilizing a clear, substantially transparent plastic material is to allow a UV curing light or gun to be directed against the composite material (held in place by the matrix) supplied to the cavity of the tooth so as to cure and harden the same in place. The matrix is intended to be removed from the mouth after the dental procedure and composite hardening process is completed and, therefore, it is extremely desirous for the material not to bind to the composite material.

The device shown in the '849 patent consists of two flat fins and a shaped middle portion. The middle portion is shaped in such a manner as to fit the upper incisors snugly at its lateral region in order to take care of proximal fillings. According to the disclosure, the two flat fins each carry an indentation leaving room for the interdental gums. During application of the die of the '849 device, the two flat fins are grasped with dental tweezers so close to the tooth that the die fits the tooth tightly when the flat fins are pressed together.

The present invention, as will be more fully described hereinafter, relates to a dental matrix of similar material to that disclosed in the '849 patent. More specifically, the present invention contemplates a central area for surrounding the tooth structure which is provided with at least one slot for cooperating with an arm or extension of similar plastic material extending from the central region. The laterally extending arm of the dental matrix of the present invention is provided with a series of ratcheting teeth which, when the free end of the arm is passed through the slot of the center area, cooperate with the slot to provide a securing and locking device which is substantially flat, i.e., at most, it is only as thick as two sheets of plastic. In this manner, adjacent teeth can be simultaneously worked upon by use of the dental matrix of the present invention. The arms are preferably of sufficient length so that independent of the tooth surface worked upon, the arms extend out the patient's mouth so as to be easily finger grippable by the dentist to secure and lock the same.

U.S. Pat. No. 4,824,365 relates to a dental matrix in a flexible strip having a tightener connected to it. The tightener is connected to the strip so as not to involve any loss of time by the dentist for each filling. The thin plastic strip has permanently applied thereto a tightener, which is easily, according to the specification, permanently deformed when pressed with the dentist's fingers or forceps in the directions of arrows 4 and 5 illustrated in FIG. 7 of the patent. The extensions 1' and 1" of the strip pass through the slit 3 of the tightener 2 and fasten at their ends to tabs 2' and 2" of the tightener by means of heat setting and then bending of the tabs to avoid injuring the patient's cheek. Thus, when the dentist presses the curved sides of the tightener, the slit 3 slips like a sliding mechanism on the extensions 1' and 1", forcing the loop 1 to become smaller and to fit around the tooth so as to give the filling material the desired shape and hold it in place. Since the tightener is permanently and not elastically deformed the loop cannot return to its enlarged shape. While the device shown in the '365 patent shows a plastic dental matrix with a tightener mechanism, it should be appreciated that that mechanism is far more expensive to produce than that of the present invention which is cut from a simple and inexpensive single thin sheet of plastic film material. The dental matrix central portion and the two arm extensions are die cut from the sheet. The present invention is far simpler to manufacture, is far less expensive and, in addition, can also be used when the tooth surface to be treated is an interproximal surface, i.e., a surface immediately adjacent to another tooth surface. On the other hand, the '365 device does not appear suitable for use on interproximal surfaces since the aluminum tightener mechanism would be placed in opposed relationship to the central portion of the dental matrix and the tightener would be interfered with by the adjacent tooth.

U.S. Pat. No. 4,997,367 also relates to a dental matrix for use in restoration procedures for teeth. According to the description of this device, each of the pair of wings 16 is provided with adhesive material 17 on its inner surface 18 for attaching the pair of wings together to secure the matrix to the tooth 12. Once positioned, the wings of the matrix may be pulled and the matrix and tooth line is then inspected to determine if any trimming is necessary. If no trimming is required, the matrix may be pulled labially so that it fits loosely about the tooth with the flange thereof inserted subgingivally. Again, the present invention, in contrast to that of the '367 patent, is significantly less expensive to manufacture, is easier to use and requires only a single sheet of plastic material from which the central portion of the matrix and the laterally extending arms are die cut. The device of the '367 patent, on the other hand, requires, in addition to the wings and the center portion 14, adhesive and backing sheets to be coated on the wings for securement of the wings to one another. The present invention is believed to be a significant and patentable advance over this prior art.

U.S. Pat. No. 4,553,937 relates to a tooth matrix band. According to the specification, the band has a central portion of a thickness of about 0.3 millimeters bounded on top by a semi-curved arcuate edge 12 and on bottom by an undulating longitudinal edge 13. An end portion or tab 14 of a height less than the central portion is formed with a slot 15 which lies generally vertically along a generatrix of a tooth which is intended to be encircled by the band. The length of the slot 15, according to the specification, corresponds essentially to the width of the tongue 16 formed and extending from the opposite end thereof. A row of teeth 17 is formed on the tongue 16 and both end portions are provided with holes 18 and 19 which are intended to be acted upon by a device (shown in FIG. 6) for tightening the dental matrix about the tooth. FIG. 4 shows, in enlarged cross section, the manner by which the teeth 17 project outwardly above the planar surface of the center portion 11 (partially shown) of the dental matrix. According to the specification of the '937 patent, the teeth 17 cooperate with the slot 15 to prevent the dental matrix from loosening during a dental procedure.

The present invention, on the other hand, provides a dental matrix positioning, retention and locking mechanism having a ratcheting feature which allows the dentist to manually selectively tighten the central portion about the tooth. The ratcheted teeth of the lateral arms are in the same physical plane as the central area (when the device is flat) so that the overall thickness of the device when in use is substantially thin and the ratchet and holding mechanism does not project far above the planar surface of the central area. In this manner, i.e., by providing the positioning, retention and locking mechanism coplanar with the surface of the central area, two adjacent teeth can be simultaneously worked upon with each tooth having a dental matrix held thereon. The ratchet teeth will not interfere with one another. In addition, by utilizing the ratchet teeth in the same plane as the central area (when the device is flat) the present invention can be very simply die cut from single sheets of thin plastic material whereas the device of the '937 patent necessarily is more complicated to manufacture and more expensive. The teeth 17 of the '937 patent are more expensive to manufacture.

U.S. Pat. No. 4,024,643 shows another embodiment of a dental matrix retainer. This device is in the form of a longitudinally split band having separate band portions for looping about the axially or gingival contour of a tooth and about the axially outer or cusp contour of the tooth. The two adjacent band portions have opposed semicircular cutouts notches 16, 18 in alignment with one another for cooperating together to define a single aperture through which the filling material may protrude into contact with an adjacent tooth. After appropriate drying or curing, the two band portions can be individually and sequentially separated and removed from between the teeth without disturbing the adjacent tooth contact. A detente 24 for each of the longitudinal bands 12 and 14 cooperates with the slot 22 to secure the device in place about a tooth, the circumferential dimension of the matrix being defined by in which slot the band and the detente is placed.

Here, again, similar to the device of the '937 patent, the detente 24 extends above the planar surface of the otherwise flat sheet and, therefore, it is more expensive to manufacture and, in addition, it serves to inhibit utilization of two of the devices on two adjacent teeth. The present invention, on the other hand, is extremely inexpensive and easy to manufacture from a single flat sheet of plastic material. The positioning and locking mechanism, the ratchet teeth on the longitudinal arms and the cooperating slot, are in the same plane as in the central portion of the matrix (when flat) and, therefore, no additional thickness of material is encountered.

U.S. Pat. No. 713,273 relates to a dental matrix crown which is intended as a permanent structure and a part of a decayed tooth. This device comprises two pivoted portions preferably made from metal which are adapted to encircle the remaining tooth structure. A cap 6 is intended to be placed on the top of the tooth or crown and held in place by a loop (See FIG. 1) or a post imbedded into the composite material. Clearly, the device of the '273 patent is quite different from the present dental matrix made from a single sheet of thin, substantially transparent plastic material which, in its prior-to use form is substantially flat.

U.S. Pat. No. 1,669,231 shows a matrix band structure. The band, according to its specification, is a thin band of sheet metal. During use, the band of the '231 patent is held in place around the tooth by an instrument indicated generally as in FIG. 4. The present invention, on the other hand, is intended to be held and locked in place without the need of any additional instruments and, indeed, the retention and locking mechanism of the present invention, integral with the central area and longitudinal arms of the dental matrix is very simple and inexpensive.

U.S. Pat. No. 2,035,135 relates to a band for dental use and comprises a metal strip which is intended to completely encircle the tooth and form a band which may be drawn tightly about the tooth and shaped to conform to the tooth without the need for a separate clamp. The metal strip consists essentially of an encircling strap portion of substantially uniform width having an enlargement holding end 16 forming a head or buckle which is provided with longitudinally spaced slots which cooperate together to form a bar 19 between them. The band is positioned over and around the tooth and by suitable instruments drawn tightly about the tooth. Then the ears 20 and 21 are folded tightly down against the strap 19 so as to prevent any movement of the band toward enlargement of its encircling size.

Again, the present invention, in contrast, is intended to be made from thin substantially transparent plastic, not metal and is provided on its longitudinally extending arms with ratcheting teeth in the plane of the central area which serve to position and lock the central matrix portion of the device about the tooth structure. The ratchet teeth cooperate with slits cut through the central matrix so that the device will not accidentally loosen or enlarge unless and until the dentist actually cuts the same off of the patient's tooth.

U.S. Pat. No. 1,255,109 shows another dental matrix band. The device shown therein is quite similar to that shown in U.S. Pat. No. 2,035,135. In the '109 patent, the device is again comprised of a thin metallic strip which is intended to be passed around the tooth and secured into position by passing the free end of the band through a slot formed in the opposite end, the free end then being bent backwardly and secured in place by the ear 16 and 17 being folded downwardly over the band. The previous comments made with respect to the '135 patent and the manner by which the present invention patentably distinguishes therefrom are equally applicable with respect to the device shown in the '109 patent.

U.S. Pat. No. 3,795,981 shows a dental retainer which is used as a clamp to secure a band of a matrix variety in position around a tooth. Here, again, the use of a separate retainer or clamping device for the metal band is required. In contrast, the present invention contemplates that the central area be made from thin, substantially transparent plastic material which is not held in position by any additional mechanism but, rather, the extending arms provided with ratchet teeth, cooperate with slits cut in the central portion to define a retention and locking mechanism. Furthermore, as is described in the specification of the '981 patent, ribs 23 of the matrix 24 project upwardly above the surface of the band and are gripped by inside surfaces of the retainer clamp. The present invention, as will be described, contemplates that the ratchet teeth of the lateral arms lie in the same plane as the central area of the matrix. They do not project above the surface of the central area and, in this manner, two of the dental matrices provided by the present invention can be used on adjacent teeth without interference of the locking mechanism with one another.

U.S. Pat. No. 3,829,975 also relates to a dental matrix band and an associated clamping device. Here too, the matrix band 10 is made of a flat flexible metallic strip and is secured in place by a separate, clamping mechanism. In accordance with the '975 device a clamp member 12 is provided to engage over the end tabs of the metal matrix band. The clamp permits the band to be drawn tightly about a tooth and locked in position. The clamp member may be formed of any suitable plastic material and has a generally rectangularly shaped opening 16. Again, use of the device shown in the '975 patent would not be suitable for adjacent teeth at the same time since the locking mechanisms might interfere with one another or, at the very least, might crowd the patient's mouth. It also is physically separate from the band and certainly more expensive to manufacture than the present device.

The present invention, on the other hand, is easily capable of being used on adjacent teeth even where the tooth surfaces to be worked upon are interproximal tooth surfaces of adjacent teeth. This is because the present invention provides a retention and locking mechanism which is integrally formed with the central area. The ratchet teeth are located in the same plane as the center area of the matrix. When placed in use the retention and locking mechanism is thin enough so that two or more of the present inventions can be used on adjacent teeth with the arms of the matrices passing through the interproximal spaces between the adjacent teeth. This is a significant and patentable advantage of the present invention.

U.S. Pat. No. 3,854,210 also relates to a dental matrix and a retainer or clamp therefor. The end portions of this matrix are brought into surface to surface contact with the exterior surface of each of the end portions being provided with a plurality of ribs, the ribs projecting outwardly and above the planar surface of the center band. The ribs are provided for engagement by the separate retainer mechanism 12. The comments and manner by which the present invention distinguishes from that of the '210 device is quite similar to the comments and manner of distinguishing the present invention from U.S. Pat. No. 3,795,981. Further comments are believed to be unnecessary.

U.S. Pat. No. 4,303,389 shows a dental instrument for the clinical application of fillings for dental cavities. This matrix is formed by a band of a stainless steel, of aluminum or other suitable alloy or plastic material having a thickness in the range of about 2/100ths to 1/10th of a millimeter. The band has a central proximal portion provided with a detachable element 3 (See FIG. 3) for establishing and determining contact between the tooth and the adjacent tooth after the filling of the dental cavity. The contact element 3 is inserted in a cutout 4 formed in the central portion of the matrix. An internal anchoring member 5 is embedded in the material employed for filling the dental cavity. The contact element is intended to be left in the filling material, even after the latter has been allowed to dry and set. The '389 patent shows an entirely separate mechanism in the form of a spring-like device, 9, or "lateral coil" which holds the matrix material in place during use. The present invention, as previously mentioned, requires no separate holding or locking device and utilizes laterally extending arms having ratchet teeth integral with the central area which cooperate with slits also in the central area of the matrix for retaining and locking the dental matrix in position.

U.S. Pat. No. 4,720,264 relates to a tool for use in and connection with tightening a dental matrix about a tooth structure as shown in FIGS. 16, 17, and 17A, the winding head 9 is fixed to the collet 2 which in turn is fixed to the flexible sleeve 4. The winding head has a cross section similar to a fluted star-like formation with sharpened flute edges 75. The winding head tapers in the form of a truncated cone and is insertable into the inner core diameter of a winding coil 60 to rotate the windable coil thereby causing it to wind and tighten around the winding head 9 and to draw material from the matrix 62, under the loop lock 64 and onto the coil 60. As can be seen ba a review of that patent, a dental matrix is thus provided. The present invention provides a retaining and locking mechanism, integral with the central portion of the dental matrix and does not require the use of any extra tools for tightening and securing the same in place.

U.S. Pat. No. 4,781,583 shows an adjustable plastic film matrix which does not require an external retainer for retaining the same on a tooth. According to the specification of the '583 patent. FIG. 3 shows a fragmentary perspective view of the lock loop retaining end of a plastic sheet member for making the matrix of that invention and illustrates an elongated laminate. While the device of the '583 patent does not require a separate retainer, it does require a separate tool for locking the matrix in position. FIG. 5 shows, in perspective, with portions cut away, the matrix of the '583 patent with the loop lock of FIG. 4 in an assembled condition on a tooth. The present invention eliminates the necessity of providing a separate retainer element.

U.S. Pat. No. 4,482,319 shows a matrix band. A dental inset, generally shown as element 10, is mounted to a matrix band 12, which along with the inset 10 is mounted on a tooth by use of a matrix band retainer (not shown) typically a Tofflemeyer retainer. The inset 10 when used in combination with the matrix band 12 is held about a tooth by the retainer and thereby permits a 360° matrix which adapts readily to the cervical circumference of molar teeth. The present invention, as mentioned, avoids the use of a separate retainer element.

U.S. Pat. No. 4,909,736 relates to a method of repairing a tooth utilizing a heat-shrinkable overlay around the tooth. According to the specification of the '736 patent, a quantity of soft, uncured, restorative material is packed onto the prepared site with an appropriate dental instrument. Then, a strip of the heat shrinkable overlay is wrapped around the tooth and the restorative material. The heat shrinkable overlay is, according to the specification, a light transmissive polymeric sheet comprised of polyvinyl chloride or similar material. An end portion 16 of the heat shrinkable overlay is secured onto the underlying film by cement or similar adhesive. Then, heat is applied to the tooth, the restorative material and the overlay so that the overlay sufficiently shrinks and tightens about the tooth. The invention is quite distinct from that shown in the '736 patent. A mechanical mechanism, the ratchet teeth and the slits are provided for tightening the dental matrix about the tooth. This is patentably distinct from that shown in the '736 patent.

U.S. Pat. No. 5,035,615 relates to a matrix band which is intended to permanently bond to the filling and the tooth. The matrix band is specifically composed of one of the conventional light activated filler materials. The band is intended to become an integral part of the restored tooth. There is disclosed no specific method for tightening the band about the tooth, and, therefore, the present invention represents a patentable advance thereover.

SUMMARY OF THE INVENTION

The present invention relates to a dental matrix of the clear, thin film plastic type having a central area or portion which is intended to surround the tooth structure being worked upon. The central area can be appropriately trimmed and cut so that its edges correspond to the various configurations of the different teeth within a patient's mouth. Extending laterally from the central portion, in the preferred embodiment, are a pair of arms. These are integrally die cut also from the same sheet of thin, plastic and substantially transparent material as the central area. These arms cooperate with slots cut in the central portion of the matrix so that the large surface area of the central portion can surround, in a tightly held manner, the tooth and restorative material being worked upon. The extending arms are provided with a series of ratchet teeth which cooperate with the slots. The arms can be pulled easily through the slots for tightening and, yet, once pulled to the appropriate tightness by the dentist, the matrix will not easily come loose since the one-way ratchet teeth of the arms maintain the dental matrix in a locked condition, in place. Then, after the dental restoration technique is accomplished, i.e., after the dental composite is dried or cured (the curing gun's ultraviolet light passes through the clear plastic material) the dental matrix can be easily removed from the tooth by a simple scissor cut. In the preferred embodiment of the present invention, the lateral arms are located at different heights of the central area, extending from opposite sides thereof. In this manner, substantially all of the exposed tooth structure, from gum line to tooth top edge can be tightly wrapped and covered by the central area or portion of the dental matrix.

It is a specific aspect of the present invention that the ratchet teeth of the longitudinally extending arms, which serve as a retaining and locking mechanism, for the central area or portion of the matrix, lie in the same plane as the central portion of the matrix. In this manner, the present invention is extremely inexpensive to manufacture, (it can be simply die cut from a flat sheet of material), and, further, adjacent teeth can be simultaneously worked on since the positioning and locking mechanism of the dental matrix is relatively thin, especially with respect to the prior art devices which utilize a dental matrix tightening mechanism which extends above the planar surface of the central area. As discussed in connection with the prior art, those devices inhibit the ability of the dentist to work on adjacent teeth, simultaneously, since the raised, above-the-planar-surface mechanisms would abut against adjacent dental matrices of similar configuration. The present invention, however, allows for adjacent teeth to be simultaneously worked upon by the dentist. The arms of the present invention extend from the central portion a sufficient distance that the dentist can always grip the free ends outside of the patient's mouth to tighten and lock the same.

BRIEF DESCRIPTION OF THE DRAWINGS

FIG. 1 is a perspective view of the preferred embodiment of the dental matrix of the present invention.

FIG. 2 is a partial perspective of a patient's mouth showing three teeth and a gum line and showing two matrices of the present invention in use, one matrix having its central, composite contacting area on the front of the tooth (tooth on the left) and the other matrix with the central portion overlying a cavity and composite material located on the back (lingual) surface of the tooth (the middle tooth).

DETAILED DESCRIPTION OF THE DRAWINGS AND THE PREFERRED EMBODIMENT

As shown in the drawings, a dental matrix 10 is die-cut from a thin sheet of substantially transparent plastic material. The material previously used for dental matrices of the plastic and flexible type is ideally suited for use in the present invention. It is important for the plastic material to be substantially transparent so that the light transmitted by a U.V. curing gun can easily pass through the dental matrix so as to cure the dental composite which is placed into the drilled out cavity of the patient's tooth. After the patient's tooth has been first filled with the composite material, the dental matrix secured thereto, and then after curing and drying of the composite material, the dental matrix can be easily cut away and removed from the patient's mouth and discarded.

The dental matrix 10 basically comprises a central area or tooth-engaging portion 12 and a pair of longitudinally extending arms 14 and 16 extending away from the central portion 12. In the preferred embodiment of the present invention, one longitudinal arm 14 extends from one side (at the top) of the central portion 12 while the other longitudinal arm 16 extends from the other side (at the bottom) of the central portion 12. Of course, it will be appreciated to those of ordinary skill in the art that the present invention can also have both longitudinally extending arms 14 and 16 extending from the same side of the central portion 12, without departing from the scope of the present invention.

According to the preferred embodiment of the present invention, the sides 18 and 20 of the central portion 12 are substantially parallel to one another. As will be appreciated by those of skill in the art, embodiments of the present invention contemplate that the sides 18 and 20 as well as top edge 22 and bottom edge 24 can be shaped to conform to the tooth and gum line being worked upon. In the basic embodiment shown, top edge 22 and bottom edge 24 are parallel to one another and are intended, during use of the dental matrix, to extend above the top surface of the tooth and to correspond to the contour of the tooth as it passes along the gumline on the bottom edge 24. Here, too, the specific shape and geometry of the top and bottom edges, 22 and 24, respectively, are dictated by the specific tooth structure sought to be wrapped and it is within the contemplation of the present invention that each tooth type have a separate and specifically shaped central portion 12 substantially corresponding to the geometry of the tooth sought to be worked upon. In any event, however, it is also within the contemplation of the present inventor that a single generic dental matrix 10 with basic central portion 12 can be provided to the dentist with the dentist then trimming and shaping the same after determining the specific tooth to be worked upon.

The central portion 12 is also provided with a pair of slots 26 and 28 cut there through which cooperate with the longitudinal arms 16 and 14, respectively. In one embodiment the slots 26 and 28 are cut at an angle with respect to a center axis of the central portion 12 whereas in the embodiment shown in FIG. 1, the slots 26 and 28 are parallel to the vertical central axis of symmetry of the central portion 12. This, too, is dictated by the shape of the tooth worked upon.

Each longitudinal arm 14 and 16 is provided with a set of ratchet teeth. The length of the arms is to be such that even if a rearwardly located tooth is being worked upon, the free ends of the arms can extend forwardly so as to be grippable by the dentist. After tightening, as will be explained, the ends of the arms can be trimmed so as not to evoke a "gag reflex" in the patient. The ratchet teeth 30 and 32 cooperate with the slots to allow easy movement of the longitudinal arms in one direction, i.e., the longitudinal arms slide through the slots 26 and 28 for tightening of the dental matrix around the tooth structure and, yet, the width of the slots with respect to the width of the base (50 for tooth 30) of the ratchet teeth is such that the longitudinal arms can not be easily removed from the slots unless and until intentional manipulating force is put on the longitudinal arms or, alternatively, as intended, the dentist cuts the matrix with scissors.

As previously discussed with reference to the prior art, it is a specific aspect of the present invention that the ratchet teeth, cooperating with the slots, lie in the same plane as the central matrix, i.e., the ratchet teeth do not extend above or below the planar level of the top nor the bottom of the central portion 12. Stated another way, the base 50 of the tooth 30, defined by points 31, 33 of the tooth 30 lies in the same plane as the tooth 30, the longitudinal arm 14 and the control area 12. Of course, this coplanar aspect of the invention relates to the configuration of the product when it is flat, i.e., before use. In this manner, a dental matrix made according to the present invention can be simultaneously used on two adjacent teeth without the ratchet teeth of the matrices abutting against one another.

The entire dental matrix 10 including the longitudinal arms, the slots, and the ratchet teeth, can be easily die cut from a single flat sheet of plastic material and, in this manner, the present invention is extremely inexpensive and easy to manufacture.

In use, the tooth of the patient to be worked upon is first selected and the dentist performs all of the necessary procedures to prepare the tooth for acceptance of dental composite or restorative material. The dentist then "works in" the composite material or dental restorative material into the tooth structure, i.e., by forcing the same into the drilled out cavity. Then, the dental matrix of the present invention is installed such that the central portion 12 overlaps the composite or restorative material. The arms are then wrapped around the tooth structure with the free ends 38 and 40 of the respective arms then inserted into the respective slots 28 and 26 of the central portion 12. Alternatively, the loop of the matrix can be formed outside of the mouth and then placed over the tooth. Then, the dentist either using his fingers or dental tweezers pulls the longitudinal arms through the slots until the central portion is tightened around the tooth structure with the bulk of the central portion 12 overlaying the restorative material. If desired, prior to utilizing the curing gun for the composite material, the dentist can trim the central portion as well as the longitudinal arms so as to minimize discomfort to the patient.

As previously described and as will be fully understood by a review of the drawings and this description of the invention, thé arms can be easily drawn through the slots since the slots allow easy one-way movement of the ratchet teeth in the tightening direction. Yet, as will be easily understood by those of ordinary skill in the art, the longitudinal arms are not easily removed from the slots unless intentionally manipulated. This is because of the relative dimensions of the base 50 of a ratchet tooth 52 in comparison to the length of the corresponding slot 28.

With the dental matrix in place, wrapped around teeth T1 and T2 and the composite material, the dentist can then apply the ultraviolet curing gun until the composite material appropriately dries and cures. Then, the dental matrices can be easily removed (by cutting with scissors) from the teeth and discarded.

While the present invention has been described with a preferred embodiment, other variations of the invention will be apparent to those of ordinary skill in the art without departing from the scope of the invention that is set forth in the appended claims.

I claim as follows:

1. A dental matrix comprising:
   (a) a central portion made of a thin film having a length and height of about that of a patient's tooth: and
   (b) one-way central portion retention and locking means extending outwardly from said central portion for securing said central portion about a patient's tooth, said locking means comprising a slot cut through said dental matrix and a first longitudinal arm extending outwardly from a first side of said central portion, said arm having a series of ratchet teeth lying in the same plane as said central portion.

2. A dental matrix as claimed in claim 1 wherein said central portion is provided with a second one-way central portion retention and locking means.

3. A dental matrix as claimed in claim 2 wherein said second one-way central portion retention and locking means comprises a second slot cut through said central portion and a second longitudinal arm extending outwardly from a second side of said central portion, said second side being opposite said first side, and said second longitudinal arm also having a series of ratchet teeth lying in the same plane as said central portion.

4. A dental matrix as claimed in claim 1 wherein the length of said slot is less than the length of the base of said ratchet teeth.

5. A dental matrix as claimed in claim 1 wherein said central portion has a top and bottom edge shaped to conform to the gum line and surface contour of the tooth to be worked on.

6. A dental matrix as claimed in claim 1 wherein said central portion is substantially transparent.

7. A dental matrix as claimed in claim 1 wherein the cumulative thicknesses of said central portion and said longitudinal arm is less than one half the distance between adjacent teeth of an average patient.

8. A dental matrix as claimed in claim 1 wherein said slot is located in said central portion.

9. A dental matrix as claimed in claim 1 wherein the length of said longitudinal arm is sufficient so that independent of the tooth or the surface of the patient's tooth being worked upon, said longitudinal arm may pass through said slot and extend forwardly out of the patient's mouth.

* * * * *